(12) United States Patent
Fan et al.

(10) Patent No.: US 12,252,729 B2
(45) Date of Patent: Mar. 18, 2025

(54) ENZYMATIC ELECTRODE SYSTEM AND ITS APPLICATIONS

(71) Applicant: Oxsyns.co, Beijing (CN)

(72) Inventors: Yilin Fan, Beijing (CN); Beichen Cheng, Beijing (CN); Yu Sun, Beijing (CN)

(73) Assignee: Oxsyns.co, Beijing (CN)

( * ) Notice: Subject to any disclaimer, the term of this patent is extended or adjusted under 35 U.S.C. 154(b) by 0 days.

(21) Appl. No.: 18/419,688

(22) Filed: Jan. 23, 2024

(65) Prior Publication Data

US 2024/0409978 A1 Dec. 12, 2024

(30) Foreign Application Priority Data

Jun. 9, 2023 (CN) .......................... 202310681714.2

(51) Int. Cl.
*C12Q 1/00* (2006.01)
*A61B 5/145* (2006.01)
*A61B 5/1486* (2006.01)
*G01N 27/327* (2006.01)

(52) U.S. Cl.
CPC .......... *C12Q 1/006* (2013.01); *A61B 5/14532* (2013.01); *A61B 5/14865* (2013.01); *G01N 27/3271* (2013.01); *G01N 27/3276* (2013.01); *G01N 27/3277* (2013.01)

(58) Field of Classification Search
None
See application file for complete search history.

(56) References Cited

U.S. PATENT DOCUMENTS

| 5,122,456 A | * | 6/1992 | Bennetto | C12Q 1/005 |
| | | | | 435/14 |
| 2018/0128764 A1* | | 5/2018 | Cardosi | C12Q 1/006 |

FOREIGN PATENT DOCUMENTS

| CN | 104334740 A | 2/2015 | |
| CN | 106442681 A | 2/2017 | |
| CN | 106957887 A | 7/2017 | |
| WO | WO-2009073927 A1 * | 6/2009 | ............. B82Y 15/00 |

* cited by examiner

*Primary Examiner* — J. Christopher Ball
(74) *Attorney, Agent, or Firm* — Nitin Kaushik

(57) ABSTRACT

The present application discloses an enzymatic electrode system and its applications. The enzymatic electrode system comprises a working electrode, a counter electrode, and an optional reference electrode. The working electrode includes an electrode support substrate and a conductive substrate located at the top of the electrode support substrate. The surface or interior of the conductive substrate contains oxidoreductases, coenzyme reductases, and optional coenzymes. This application utilizes a comprehensive enzymatic electrode system incorporating oxidoreductases, coenzyme reductases, and coenzymes for the detection of specific substances in samples, such as glucose, lactate, ketones, and the like.

19 Claims, 16 Drawing Sheets

ENZYMATIC ELECTRODE SYSTEM AND ITS APPLICATIONS

CROSS-REFERENCE TO RELATED APPLICATIONS

The present application claims the priority benefit of Chinese Patent Application No. 202310681714.2, titled "Enzymatic Electrode System and its Applications," filed on Jun. 9, 2023. The entire contents of the mentioned application are incorporated into the present application by reference.

TECHNICAL FIELD

The embodiments of the present application pertain to the field of enzymatic bioelectrocatalysis, specifically involving an enzymatic electrode system and its applications.

BACKGROUND

The enzymatic electrode can serve as a biosensor for detecting and quantifying specific chemical substances. For instance, the enzymatic electrode can be designed as a glucose sensor, providing rapid and quantitative blood glucose monitoring (BGM) for individual blood sugar control.

In comparison to Blood Glucose Monitoring (BGM), Continuous Glucose Monitoring (CGM) technology is more advanced, offering real-time blood glucose level information around the clock. CGM involves the use of implanted subcutaneous sensors to measure interstitial fluid glucose levels, providing continuous data that is valuable for understanding glucose trends and making timely adjustments to diabetes management plans.

Traditional BGM systems based on glucose oxidase and dehydrogenase enzymes utilize an indirect electron transfer mechanism involving electron mediators such as potassium ferricyanide (K3Fe(CN)6), ferrocene and its derivatives, quinones (such as benzoquinone and naphthoquinone), Prussian blue, methylene blue, ruthenium-based complexes, and rhenium-based complexes. However, the toxicity and susceptibility to leakage of these mediators render them unsuitable for Continuous Glucose Monitoring (CGM). The use of such mediators has impeded the progress of CGM systems. Therefore, there is an urgent need to develop a Direct Electron Transfer (DET)-based mediator-free system to enhance traditional blood glucose monitoring systems.

SUMMARY

The purpose of this application is to provide an enzymatic electrode system comprising a working electrode, a counter electrode, and an optional reference electrode. The working electrode includes an electrode support substrate and a conductive substrate located at the top of the electrode support substrate. The surface or interior of the conductive substrate contains oxidoreductases, coenzyme reductases, and optional coenzymes.

This application also discloses a detection system based on the enzymatic electrode system. The detection system comprises the enzymatic electrode system, a potentiostat for generating current within the enzymatic electrode system, and a current measurement device for measuring the current generated within the enzymatic electrode system.

The enzymatic electrode system provided in this application, and the detection system based on this enzymatic electrode system, achieve direct electron transfer (DET) through the unique binding of enzymes to the electrode surface. This facilitates direct communication between oxidoreductases, coenzyme reductases, and the electrode without the need for electron mediators. In comparison to existing technologies, the enzymatic electrode system presented in this application exhibits specific substrate selectivity (especially for glucose), is non-toxic, devoid of artificial electron mediators, stable, and has a detection limit within the human blood glucose range (0-30 mM), showcasing potential for commercial applications.

BRIEF DESCRIPTION OF DRAWINGS

In order to provide a clearer illustration of the technical solutions in the embodiments of the present application or the prior art, a brief introduction to the drawings required in the description of the embodiments or the prior art is presented below. It is evident that the drawings described below are merely exemplary embodiments of the present application, and ordinary skilled artisans in the field can obtain other drawings based on the provided drawings without the need for inventive efforts.

In FIG. 3A, the curve depicts the variation of current over time, while FIG. 3B demonstrates the relationship between the titrated glucose concentration and the corresponding reaction current.

In FIG. 4A, the titration process of glucose under anaerobic conditions is shown, while FIG. 4B illustrates the titration process under aerobic conditions. FIG. 4C demonstrates the relationship between the titrated glucose concentration and the corresponding reaction current.

In FIG. 5A, the curve depicts the variation of current over time, while FIG. 5B shows the relationship between current and concentration within the range of glucose concentrations in the simulated body fluid environment.

Figure 1:
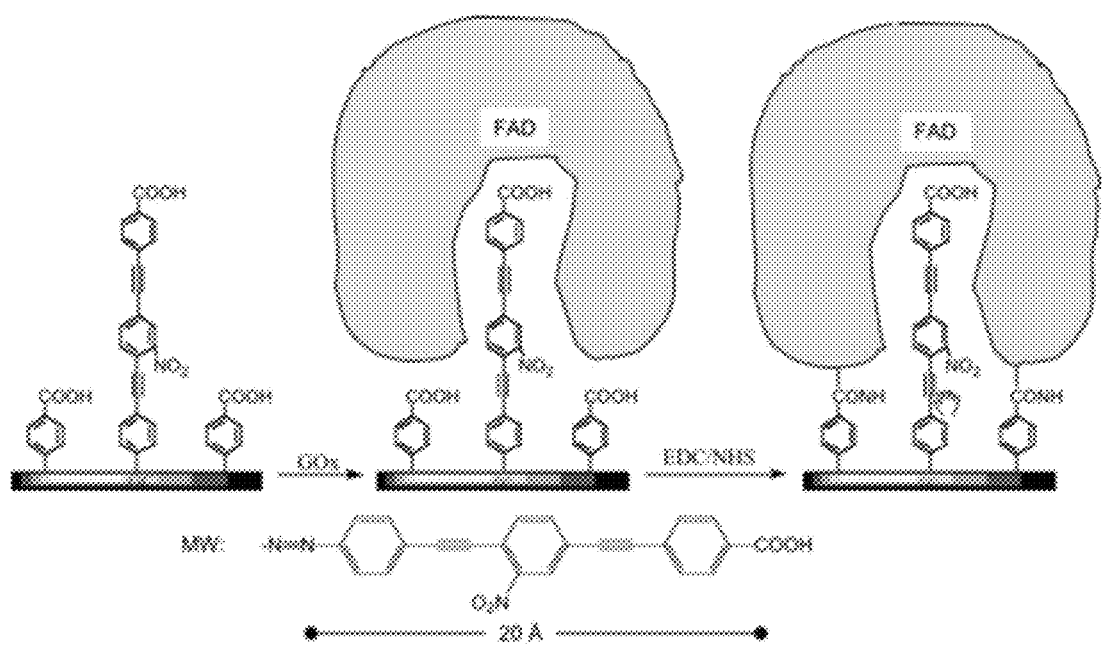
FIG. 1 depicts a schematic diagram illustrating the typical principle of the existing enzymatic glucose biosensor technology.

In the diagram:
1. Electrode support substrate; 2. Conductive substrate; 3. Coenzyme reductase (e.g., diaphorase); 4. Oxidoreductase (e.g., glucose dehydrogenase).

DETAILED DESCRIPTION OF THE EMBODIMENTS

The specific embodiments provided below further illustrate the present invention. However, it should be understood that these examples are illustrative and not intended to limit the scope of the invention. Additionally, it should be understood that, after reading the teachings of the present invention, those skilled in the art may make various changes or modifications, and such equivalent forms also fall within the scope defined by the appended claims of this application.

For convenience and clarity, some terms used in the specification, embodiments, and claims are described here.

The "glucose dehydrogenase" (GDH) mentioned in the present invention is an NAD(P)$^+$-dependent oxidoreductase that catalyzes the conversion of glucose and NAD(P)$^+$ to gluconic acid and NAD(P)H. Glucose dehydrogenase is mainly present in the liver of various microorganisms and higher animals.

The present invention provides an enzymatic electrode system comprising:
a working electrode, a counter electrode, and an optional reference electrode.

The working electrode includes an electrode support substrate and a conductive substrate located at the top of the electrode support substrate. The surface or interior of the conductive substrate contains oxidoreductase, coenzyme reductase, and optional coenzymes.

The present invention involves a working electrode with a conductive substrate. The conductive substrate is formed by screen printing a composite ink composed of base ink and an electron tunnelling agent. The base ink is a conductive paste consisting of conductive particles, binders, defoamers, and dispersants mixed in certain proportions and dispersed for a period of time. The composite ink is a mixture of nanoscale oxides and base ink in specific proportions. This composite ink is screen printed onto an electrode support substrate and then cured at a high or room temperature for a certain period to obtain the working electrode.

The conductive particles are selected from conductive carbon black, carbon nanospheres, graphite powder, graphene, carbon nanotubes, carboxylated nanotubes, hydroxylated nanotubes, etc., in a mass ratio of 10-30%, preferably 20%. The binder is one or several polymers selected from polyacrylic acid resin, epoxy ethane, polyurethane, polyaniline, in a mass ratio of 10-25%, preferably 20%. The defoamer is one or several defoaming agents selected from organosilicon defoamers, non-ionic defoamers, in a mass ratio of 0.1-3%, preferably 0.3%. The dispersant is one or several solvents selected from water, diesters, isophorone, ethanol, ethyl acetate, tetrahydrofuran, N-methyl-2-pyrrolidone, in a solvent ratio of 40-70%, preferably 50%. The dispersion is performed by high-speed stirring, with a speed of 1000-4000 rpm, preferably 3000 rpm, and a dispersion time of 0.5 to 10 hours, preferably 2 hours. The curing temperature is 25 to 80° C., preferably 60° C. . . . The drying time is 0.5 to 24 hours, preferably 10 hours. The electron tunnelling agent is a nanoscale oxide, which can be a metal or non-metal oxide or a mixture thereof. The electron tunnelling agent includes oxides such as alumina, zinc oxide, iron oxide, silicon oxide, calcium oxide, magnesium oxide, tin oxide, indium tin oxide, antimony tin oxide. Zinc oxide is preferred, and the nanoparticle size is 20-1000 nm, preferably 500-1000 nm, more preferably 500 nm. The mass ratio of base ink to the electron tunnelling agent in the composite ink is 1:1 to 100, preferably 1:45.

This enzyme electrode system allows for electron transfer between the enzyme and the conductive substrate without the need for any electron mediator. In this enzyme electrode system, direct electron transfer (DET) is achieved by adding an electron tunnelling agent, allowing electrons to move directly from the conductive layer substrate to the coenzyme reductase.

In certain embodiments of the present invention, glucose dehydrogenase (GDH) can be either a natural wild-type enzyme or a genetically modified enzyme. It includes but is not limited to NAD-dependent glucose dehydrogenase, NADP-dependent glucose dehydrogenase, FAD-dependent glucose dehydrogenase, or a mixture thereof. Enzymes with high substrate specificity (glucose), such as NAD-dependent glucose dehydrogenase and/or NADP-dependent glucose dehydrogenase, are preferred. The function of glucose dehydrogenase is to react with glucose, oxidizing it to gluconic acid and transferring electrons to the coenzyme. Simultaneously, it utilizes energy to reduce NAD(P)$^+$ to NAD(P)H.

Furthermore, glucose is transformed into gluconolactone under the catalysis of glucose dehydrogenase, and the oxidized form of NAD(P)$^+$ is reduced to NAD(P)H.

Glucose + NAD (P)$^+$ ⟶ Gluconic acid + NAD (P)H + H$^+$

Subsequently, NAD(P)H is oxidized back to the oxidized form NAD(P)$^+$ under the catalysis of the coenzyme reductase.

NAD(P)H - 2e$^-$ ⟶ NAD(P)$^+$ + H$^+$

The present invention demonstrates that the glucose dehydrogenase NAD(P)-type electron acceptor system can be used to detect glucose concentration. The unique ability of direct electron transfer in this system eliminates the need for toxic electron mediators, making it an ideal choice for glucose detection methods.

In the mentioned reaction, NAD(P) refers to NAD(coenzyme I) and NADP (coenzyme II). In some embodiments of the present invention, the coenzyme reductase, an enzyme capable of reducing coenzymes, is widely present in nature. The invention can use wild-type enzymes or genetically modified enzymes. In some embodiments, the coenzyme reductase is a flavin reductase, an enzyme that catalyzes reactions involving NADP (H) or NAD(H); preferably DI (diaphorase). Various sources of DI from protein databases have been tested in the present invention, all showing a response in current. In this invention, the role of flavin reductase is to convert the oxidized form of coenzyme I/II to the reduced form of coenzyme I/II.

In some embodiments of the present invention, glucose dehydrogenase and coenzyme reductase can be placed on the surface and inside the conductive base of the working electrode in any proportion. In non-limiting specific examples, the molar concentration ratio of glucose dehydrogenase to coenzyme reductase can be 1:100, 1:90, 1:80, 1:70, 1:60, 1:50, 1:40, 1:30, 1:20, 1:10, 1:1, 10:1, 20:1, 30:1, 40:1, 50:1, 60:1, 70:1, 80:1, 90:1, 100:1.

In one embodiment of the present invention, in the case where the test sample does not contain coenzymes, the surface or interior of the conductive substrate may also contain coenzymes. The scientific name of the coenzyme is Nicotinamide Adenine Dinucleotide (NAD(P)), also known commercially as coenzyme I/II. The coenzymes mentioned in the present invention are selected from NAD, NADP, or FAD, either individually or in combination. In the present invention, the added coenzymes can be in the oxidized state or the reduced state. Both the oxidized and reduced forms of coenzyme I/II can generate effective current. Since coenzymes naturally exist in biological fluids, including tissue fluid, cytoplasm, plasma, platelets, blood, interstitial fluid, saliva, sweat, etc., and considering the small amount of coenzyme used in the present invention, even in micromolar or pico-molar quantities, it is sufficient to facilitate the reaction. Therefore, in practical detection, if the solution already contains coenzymes, there is no need to add additional coenzymes to the enzymatic electrode.

In one embodiment of the present invention, the amount of added coenzymes is in the range of 5 pM to 50 mM, preferably $10\mu$ M to $50\mu$ M.

In some embodiments of the present invention, the surface microstructure of the working electrode can be smooth, rough, or porous. In fact, any electrode capable of immobilizing and accommodating enzymes can serve as the working electrode. For obtaining a larger current per unit area, working electrodes with porous surfaces are preferred, as they can more effectively enhance the current density per unit area.

Figure 2A:
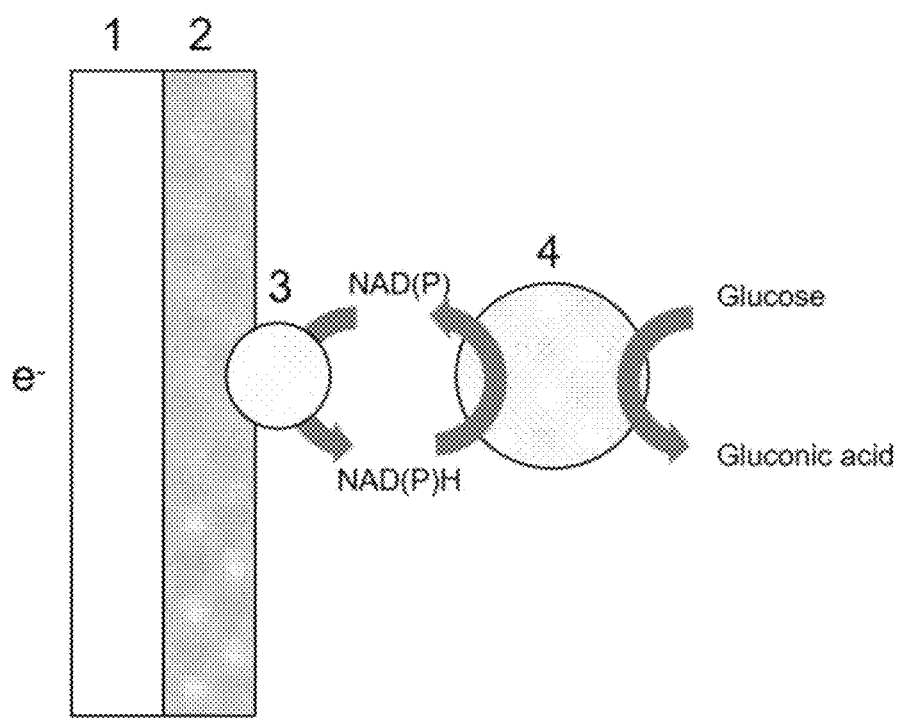
FIGS. 2A and 2B present schematic diagrams illustrating the structure and principle of the enzymatic electrode system provided in embodiments of the present invention.
Figure 2B:
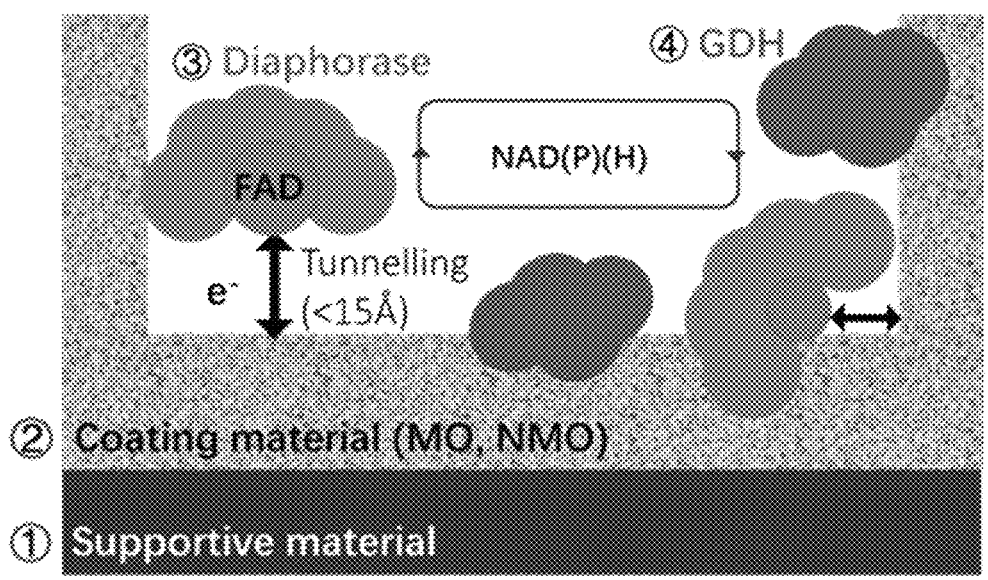

In one embodiment of the present invention, as shown in FIGS. 2a and 2b, the working electrode of the enzyme electrode system comprises an electrode support substrate 1 and a conductive substrate 2. The surface or interior of the conductive substrate 2 includes oxidoreductases 4, coenzyme reductase 3, and optional coenzymes.

The electrode support substrate 1 provides support for the electrode system during the detection process. The electrode support substrate 1 can be conductive or insulating. The electrode support substrate 1 can be made of one or more materials, including metal, bioceramics, natural materials, or synthetic polymers. Metals such as titanium and its alloys, bioceramics such as hydroxyapatite (HAp) and $\alpha,\beta$-tricalcium phosphate ($\alpha,\beta$-TCP), calcium carbonate, bioactive glass and glass ceramics, aluminum oxide, and zirconia can be used. Natural materials such as collagen, gelatin, silk fibroin (SF), chitosan, hyaluronic acid (HA), gelatin (GG), and their derivatives, as well as synthetic polymers like polyurethane (PU) and polycaprolactone (PCL), can also be used.

The hardness of the electrode support substrate 1 is not restricted. When the enzyme electrode is used in an implantable glucose meter, the electrode support substrate 1 is preferably made of a softer material to enhance comfort during wear. However, when applied to test strips, a harder material is preferred for the electrode support substrate 1.

The conductive substrate 2 can be selected from at least one of noble metal nanoparticles, nanocarbon, conductive polymers, or nanocomposite materials. Examples include ITO (Indium Tin Oxide), graphene, carbon nanotubes, gold electrodes, silver electrodes, conductive hydrogels, or conductive or semiconductive materials doped with nanoelectrodes. The conductive substrate 2 is used to immobilize or contain enzymes during the detection process, allowing electrons to flow through the conductive substrate 2 and be conducted to the enzymes. The material characteristics of the conductive substrate 2 need to possess conductivity and provide adsorption, covalent attachment, entrapment electrostatic adsorption, or a combination of these forces, allowing the enzymes to be retained on the surface and/or inside the conductive substrate 2 without loss.

The oxidoreductase 4 can be any $NAD(P)^+$-dependent oxidoreductase (including dehydrogenases) such as glucose dehydrogenase, lactate dehydrogenase, alcohol dehydrogenase, aldehyde dehydrogenase, ketone dehydrogenase, etc. This allows the detection and sensing of substances such as glucose, lactate, alcohol, aldehyde, uric acid, ketones, creatinine, and more.

The coenzyme reductase 3 is used to convert the reduced form of the coenzyme to the oxidized form, and the coenzyme serves as an electron transfer agent. The electron transfer chain in this sensing process starts from glucose in the sample and ends at the electrode system.

In some embodiments of the present invention, methods for placing glucose dehydrogenase, coenzyme reductase, and optionally coenzymes on the surface and/or inside the conductive substrate to form a conductive layer include but are not limited to adsorption, covalent attachment, entrapment electrostatic adsorption, or a combination of these forces. Preferably, glucose dehydrogenase, coenzyme reductase, and optional coenzymes are placed within the porous structure of the conductive substrate, for example, on a conductive nanolayer or within gaps formed by the nanolayer. Different combinations of support substrate materials and conductive substrate materials will result in different current densities. In various embodiments of the present invention, the range of current density is from 5 pA cm-2 to 1 mA cm-2. Different materials can be chosen based on specific application requirements.

In some embodiments of the present invention, glucose dehydrogenase, coenzyme reductase, and optionally coenzymes are co-immobilized through various adsorption, covalent attachment, entrapment electrostatic adsorption, or a combination of these forces and then attached to the surface and/or inside the conductive substrate.

In certain embodiments of the present invention, to achieve optimized electron transfer efficiency and prevent enzyme detachment, glucose dehydrogenase and coenzyme reductase are placed within the conductive substrate. Preferably, the conductive substrate has a porous structure, and more preferably, it is made of nanoporous materials. The pore diameter is around 20-100 nm, preferably around 50 nm. The thickness of the conductive substrate is in the range of 100-5000 nm, preferably 1000-3000 nm, and more preferably about 2000 nm.

The present invention also provides a method for determining the concentration of glucose in a sample, comprising:
S1. Preparing a sample solution containing glucose;
S2. Bringing the sample solution into contact with the working electrode of the enzyme electrode system, thereby generating a current through the sample solution;

S3. Calculating the concentration of glucose based on the measurement of the enzyme electrode system.

According to certain embodiments of the present invention, the method for determining glucose concentration can be applied to but is not limited to continuous glucose monitoring (CGM) devices. It can also be applied to disposable devices such as blood glucose test strips, used in conjunction with corresponding measuring instruments.

The present invention further provides a detection system comprising: an enzyme electrode system; a potentiostat for generating current in the enzyme electrode system; and a current measuring device for measuring the current generated in the enzyme electrode system.

The detection system can be used for a glucose concentration determination system in a sample, i.e., a glucose concentration measurement system. The detection system determines the glucose concentration by contacting it with a sample solution. According to some embodiments of the invention, the glucose concentration measurement system can be implantable or portable.

The enzyme electrode system provided in this application, along with the detection system based on it, achieves direct electron transfer (DET) through the unique binding of enzymes to the electrode surface. This enables direct communication between oxidoreductases, coenzyme reductases, and the electrode without the need for electron mediators. Compared to existing technologies, the enzyme electrode system presented in this application exhibits specific substrate selectivity (especially for glucose), is non-toxic, does not involve artificial electron mediators, is stable, and has a detection limit within the human blood glucose range (0-30 mM), showing potential for commercial applications.

Below, specific examples are given to introduce the enzyme electrode system provided by the present invention and its applications as a biosensor.

Reagent Source:

The NAD-dependent DI, NADP-dependent DI, NAD-dependent Glucose Dehydrogenase (GDH), and NADP-dependent GDH mentioned in the present invention are commercially obtained enzymes purchased from Sigma-Aldrich.

Example 1

Preparation of Enzyme Electrode

The NADP-type DI (4.4 µL) and the NADP-type GDH (15 µL) were mixed with 8.6 µL of pH 9 TAPS buffer, resulting in final concentrations of 0.12 mM for DI and 0.036 mM for GDH. This mixture was uniformly applied to a working electrode prepared as described in Example 5 (surface area 2.8 cm2), left to incubate for 25 minutes, then rinsed with pH 9 TAPS buffer to wash off the surface enzyme solution, obtaining a working electrode plate loaded with DI and GDH.

Using the above-mentioned DI and GDH-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of pH 7.4 simulated body fluid SBF (composition: NaCl 135 mM, KCl 5 mM, $MgCl_2$ 1.5 mM, $CaCl_2$) 2.5 mM, $Na_2HPO_4$ 1 mM, $Na_2SO_4$ 0.5 mM, $NaHCO_3$ 4.2 mM, Tris 5 mM), with an additional 5 µM of coenzyme $NADP^+$ added.

Detection of Glucose Concentration (0-15 mM) in a Near-Human Serum Environment

Figure 3A:
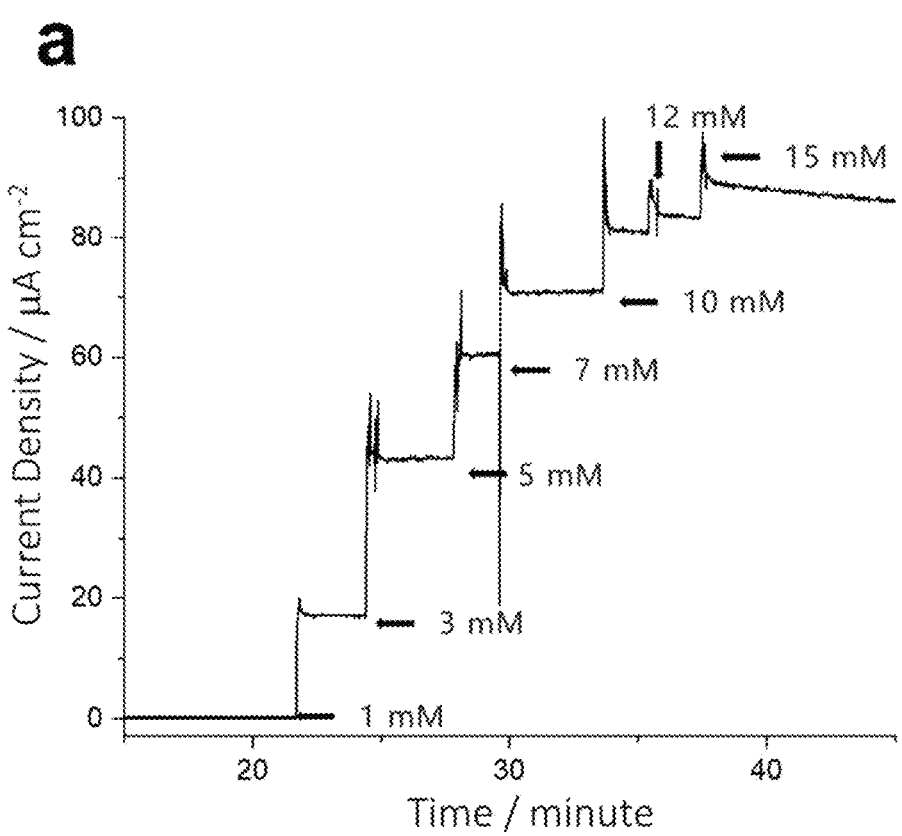
FIGS. 3A and 3B illustrate the titration detection of glucose concentration (0-15 mM) in a simulated body fluid environment using the DI-GDH enzymatic electrochemical system provided in embodiments of the present invention.
Figure 3B:
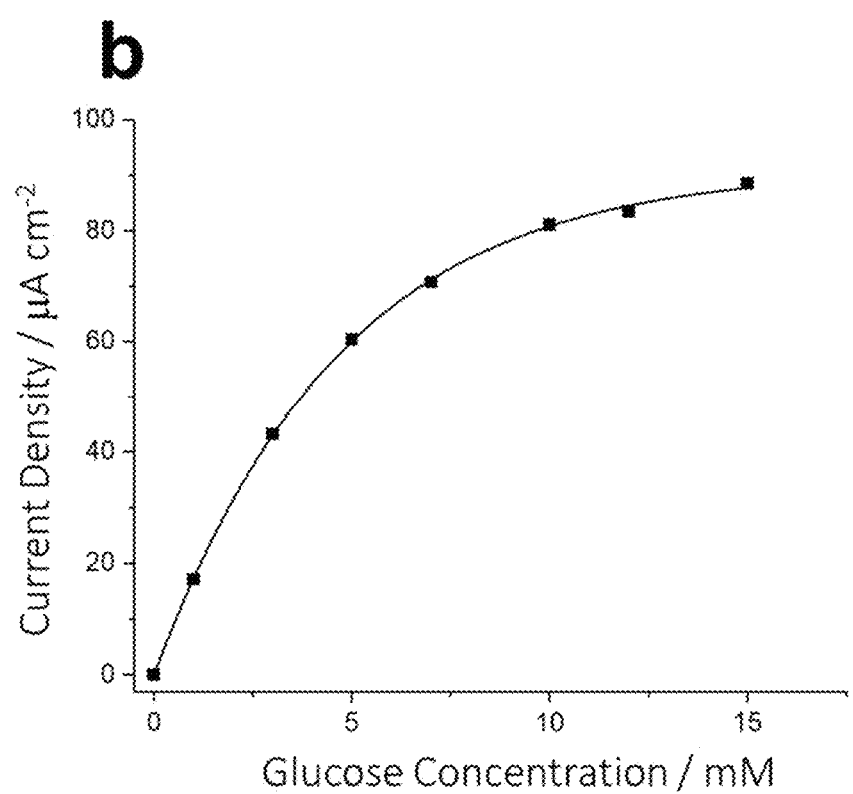

The three-electrode electrolytic cell described in Example 1 was placed in an anaerobic glove box. Under the control of Ivium electrochemical workstation, a constant voltage scan at −0.2 V was conducted, with magnetic stirring at 800 rpm. After the reaction started and the current stabilized, a concentrated glucose solution was added using a syringe for titration, increasing the glucose concentration in the reaction liquid from 0-15 mM. The change in reaction rate was reflected by the reaction current, corresponding to the change in glucose concentration. The process is shown in FIG. 3, where FIG. 3A displays the curve of current change over time, with the magnitude of current reflecting the rate of reaction. This reaction is a glucose oxidation reaction; a more positive current indicates a higher glucose reaction rate, corresponding to a higher glucose concentration. FIG. 3B plots the relationship between titrated glucose concentration and reaction current; this graph reflects a good correspondence between current and concentration within the glucose concentration range in the simulated body fluid environment.

Comparison of Working Conditions in Aerobic and Anaerobic Environments

Figure 4A:
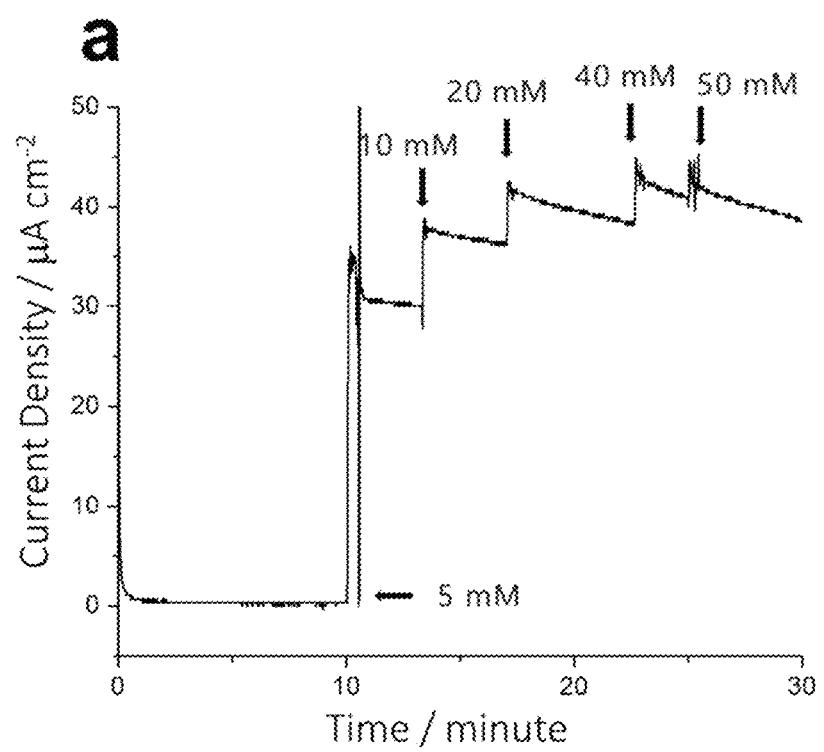
FIGS. 4A, 4B and 4C compare the titration detection of glucose in aerobic and anaerobic environments.
Figure 4B:
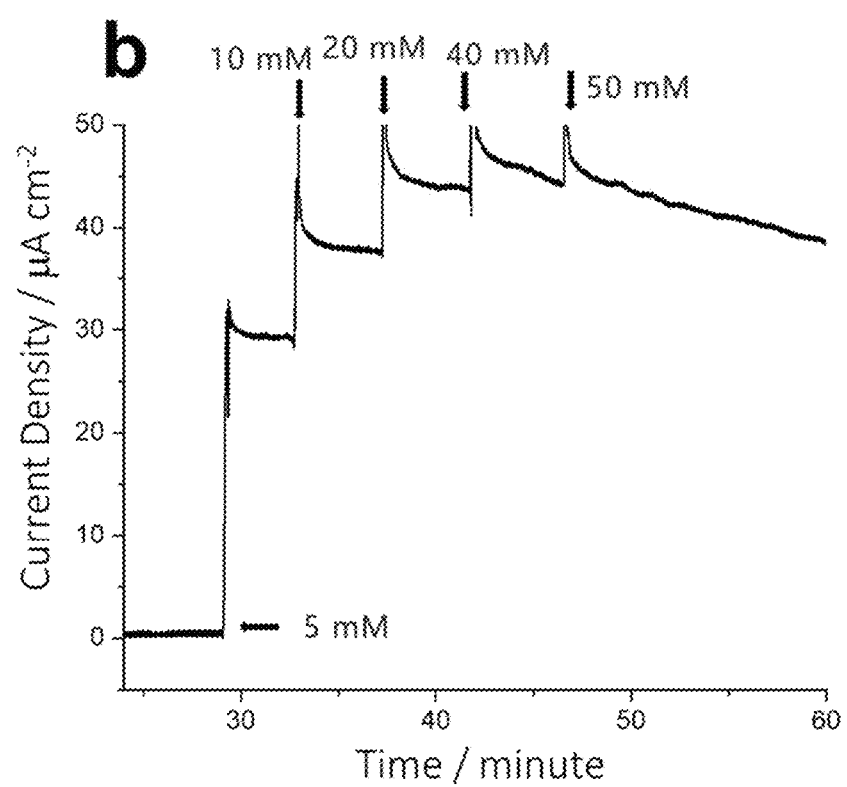
Figure 4C:
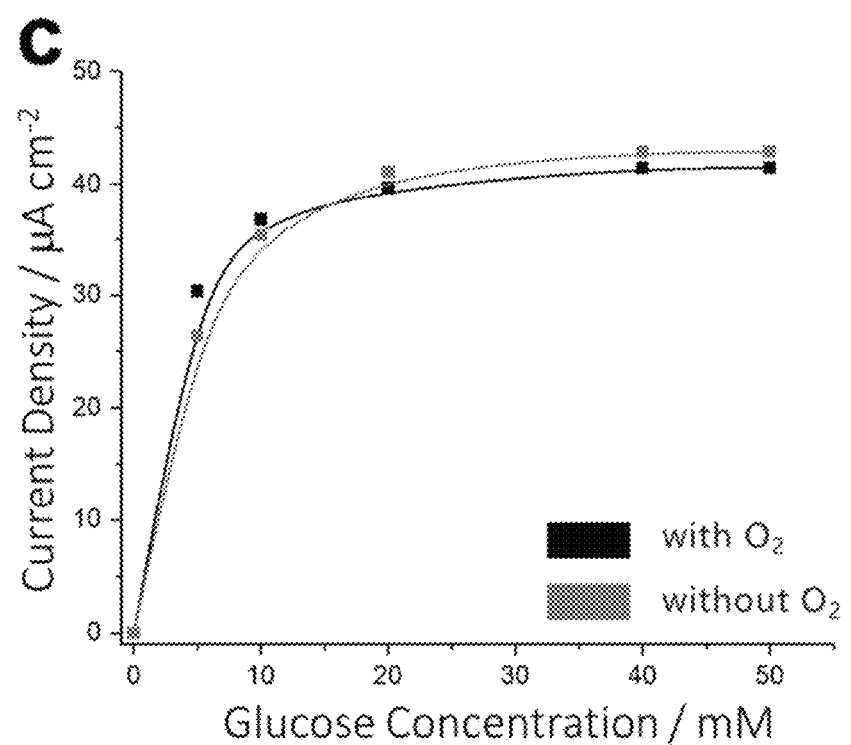

The three-electrode electrochemical reactor described in Example 1 was placed in both an anaerobic glove box and in air for reaction. Under the control of Ivium electrochemical workstation, a constant voltage scan at −0.2 V was conducted, with magnetic stirring at 800 rpm. After the reaction started and the current stabilized, a concentrated glucose solution was added using a syringe for titration, increasing the glucose concentration in the reaction liquid from 0-50 mM. The change in reaction rate was reflected by the reaction current, corresponding to the change in glucose concentration. The process is shown in FIG. 4, where FIG. 4A is the glucose titration process in an anaerobic environment, and FIG. 4B is the process in an aerobic environment. The magnitude of the current reflects the rate of glucose oxidation reaction; a more positive current indicates a higher glucose reaction rate, corresponding to a higher glucose concentration. FIG. 4C shows the relationship between titrated glucose concentration and reaction current. The comparison shows that the presence of oxygen has almost no effect on the monitoring capability of the system, with only a slight background current from oxygen reduction, which can be deducted as a baseline. This experiment proves that the glucose detection system of this invention is not affected by oxygen concentration, thus avoiding detection errors.

Example 2

Preparation of Enzyme Electrode:

The NADP-type DI (1.5 µL) and the NADP-type GDH (28.5 L) were mixed to achieve final concentrations of 0.04 mM for DI and 0.068 mM for GDH. This mixture was uniformly applied to a working electrode prepared as described in Example 5 (surface area 2.8 cm2), left to incubate for 25 minutes, then rinsed with pH 9 TAPS buffer to wash off the surface enzyme solution, obtaining a working electrode plate loaded with DI and GDH.

Using the above-mentioned DI and GDH-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of pH 7.4 simulated body fluid SBF (composition: NaCl 135 mM, KCl 5 mM, $MgCl_2$ 1.5 mM, $CaCl_2$) 2.5 mM, $Na_2HPO_4$ 1 mM, $Na_2SO_4$ 0.5 mM, $NaHCO_3$ 4.2 mM, Tris 5 mM), with an additional 5 µM of coenzyme $NADP^+$ added.

Figure 5A:
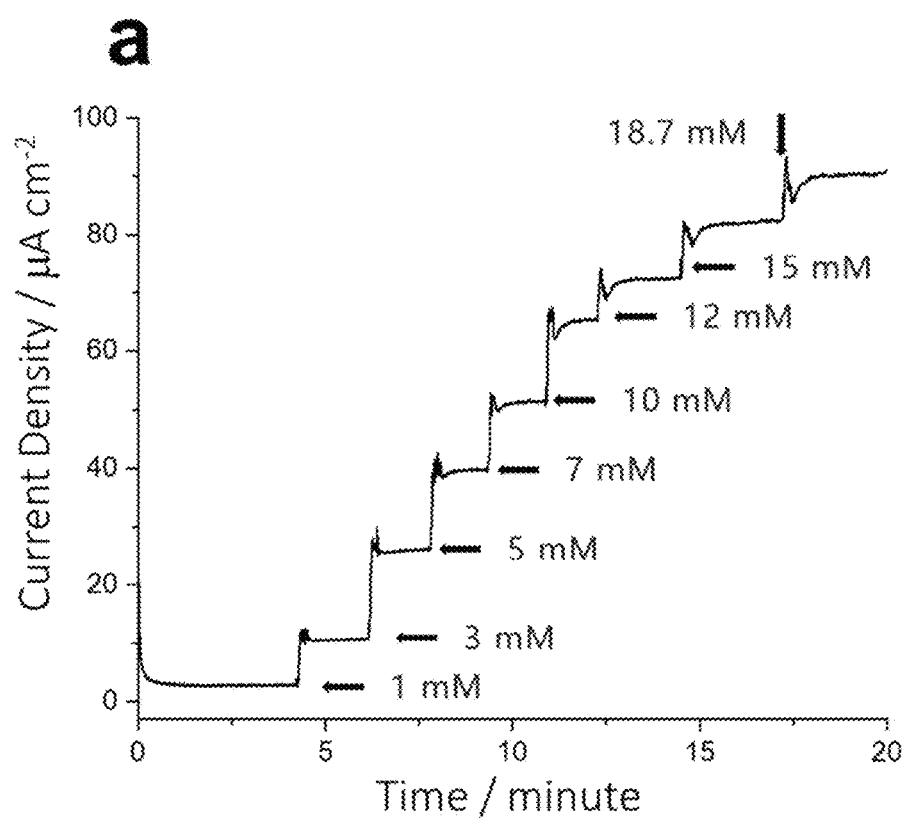
FIGS. 5A and 5B illustrate the titration detection of glucose concentration (0-15 mM) in a simulated body fluid environment using the DI-GDH enzymatic electrochemical system provided in embodiments of the present invention.
Figure 5B:
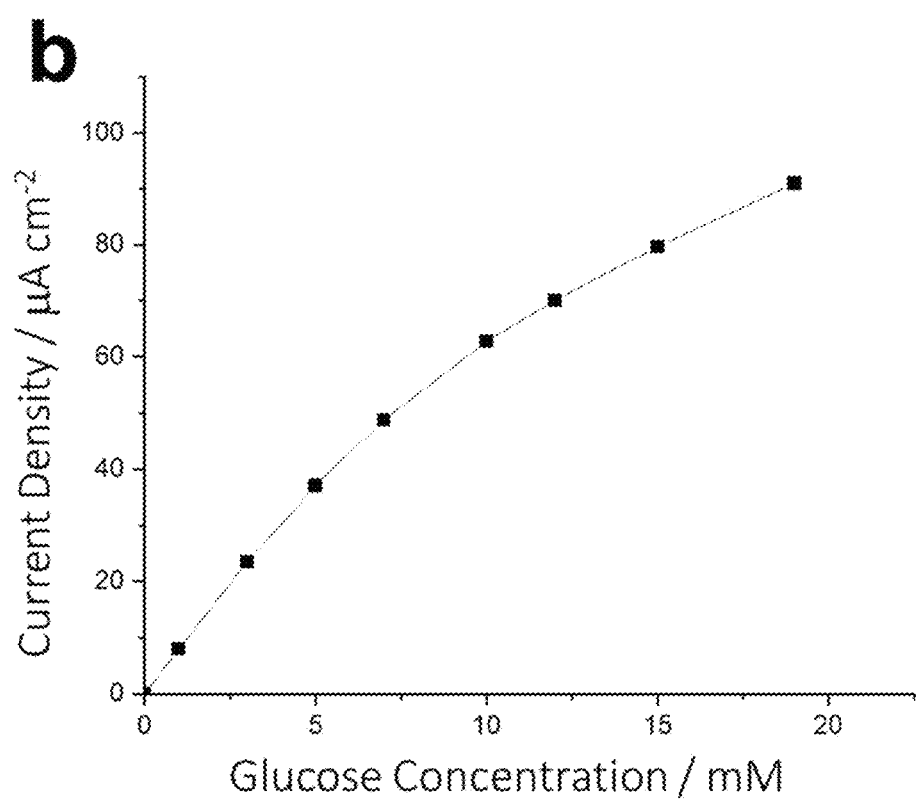

Detection of Glucose Concentration (0-15 mM) in a Near-Human Serum Environment:

The three-electrode electrolytic cell described in Example 2 was placed in an anaerobic glove box. Under the control of Ivium electrochemical workstation, a constant voltage scan at −0.1 V was conducted, with magnetic stirring at 800 rpm. After the reaction started and the current stabilized, a concentrated glucose solution was added using a syringe for titration, increasing the glucose concentration in the reaction liquid from 0-15 mM. The change in reaction rate was reflected by the reaction current, corresponding to the change in glucose concentration. The process is shown in FIG. 5, where FIG. 5A displays the curve of current change over time, with the magnitude of current reflecting the rate of reaction. This reaction is a glucose oxidation reaction; a more positive current indicates a higher glucose reaction rate, corresponding to a higher glucose concentration. FIG. 5B plots the relationship between titrated glucose concentration and reaction current; this graph reflects a good correspondence between current and concentration within the glucose concentration range in the simulated body fluid environment.

Example 3

Preparation of Enzyme Electrode

The NADP-type DI (1.8 µL) and the NADP-type GDH (10.2 µL) solution were mixed to achieve final concentrations of 0.048 mM for DI and 0.024 mM for GDH. The mixture was drop-coated onto a nano-gold-coated C electrode (surface area 0.2 cm$^2$), left to incubate for 5 minutes, then rinsed with pH 9 TAPS buffer to wash off the surface enzyme solution, obtaining a nano-gold-coated electrode loaded with DI and GDH.

In the screen-printed three-electrode system, the nano-gold-coated electrode loaded with DI and GDH was used as the working electrode, a carbon electrode as the counter electrode, and Ag/AgCl (3 M KCl) as the reference electrode. Two solutions were pre-prepared: Solution 1 contained pH 7.4 simulated body fluid SBF (composition: NaCl 135 mM, KCl 5 mM, $MgCl_2$ 1.5 mM, $CaCl_2$) 2.5 mM, $Na_2HPO_4$ 1 mM, $Na_2SO_4$ 0.5 mM, $NaHCO_3$ 4.2 mM, Tris 5 mM) and 5 µM of coenzyme $NADP^+$; Solution 2 was 15 mM glucose dissolved in Solution 1.

Experiment on Simulating Glucose Concentration Changes on Screen-Printed Electrode The enzyme electrode system described in Example 2 was tested in air. Under the control of the Ivium electrochemical workstation, a constant voltage scan at −0.2 V was conducted. After the reaction started and the current stabilized, multiple additions of Solution 1 and Solution 2 were performed, with reaction rate changes reflected by the reaction current, corresponding to glucose concentration changes. The specific procedure was as follows:
  a) Adding Solution 1 to the electrode system once, standing still until it stabilized, simulating a no-glucose situation and observing background current;
  b) Adding Solution 2 to the electrode system once, simulating the presence of glucose, where the current increased and then gradually decreased, reflecting glucose consumption through reaction;
  c) Adding Solution 2 to the electrode system once to replenish glucose;
  d) Continuously adding Solution 2, simulating a fluid flow that continuously supplies a stable concentration level of glucose;
  e) Adding Solution 1 to rinse, simulating a decrease in glucose concentration;
  f) Adding Solution 2 to the system once, simulating an increase in glucose concentration;
  g) Adding Solution 1 to rinse, simulating a decrease in glucose concentration again.

Figure 6:
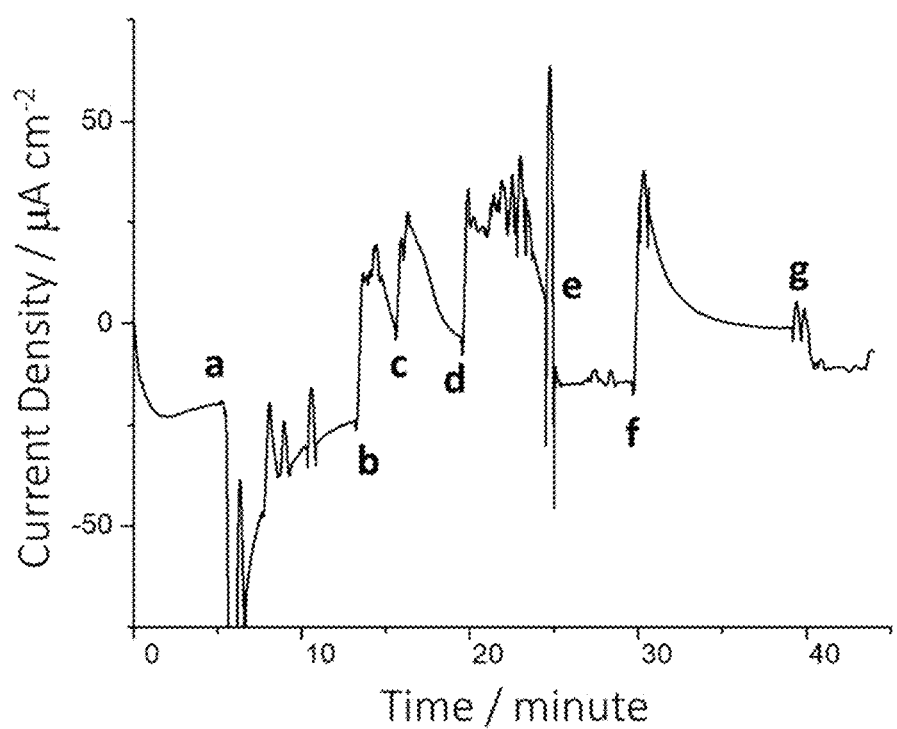
FIG. 6 presents the timed current records simulating the variation of glucose concentration on a microelectrode using the DI-GDH enzymatic electrochemical system provided in embodiments of the present invention.

The process of simulated glucose concentration changes in the system was recorded using the chronoamperometry method, as detailed in FIG. 6. FIG. 6 shows the testing process of the flow system under real-time dynamic changes of glucose, proving the feasibility of this system for glucose monitoring.

Example 4

Preparation of Enzyme Electrode

The NADP-type DI (2.2 µL), NAD-type DI (2.2 µL), NADP-type GDH (7.5 µL) and NAD-type GDH (7.5 µL) and 8.6 µL of pH 9 TAPS buffer were mixed, resulting in final concentrations of 0.12 mM for DI and 0.036 mM for GDH. This mixture was uniformly applied to a working electrode prepared as described in Example 5 (surface area 2.8 cm$^2$), left to incubate for 25 minutes, then rinsed with pH 9 TAPS buffer to wash off the surface enzyme solution, obtaining a working electrode plate loaded with a mix of NAD/NADP-dependent DI and GDH.

Using the above-mentioned DI and GDH-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of pH 7.4 simulated body fluid SBF (composition: NaCl 135 mM, KCl 5 mM, $MgCl_2$ 1.5 mM, $CaCl_2$) 2.5 mM, $Na_2HPO_4$ 1 mM, $Na_2SO_4$ 0.5 mM, $NaHCO_3$ 4.2 mM, Tris 5 mM), with an additional 2.5 µM of coenzyme $NADP^+$ and 2.5 µM of coenzyme $NAD^+$ added.

Figure 7:
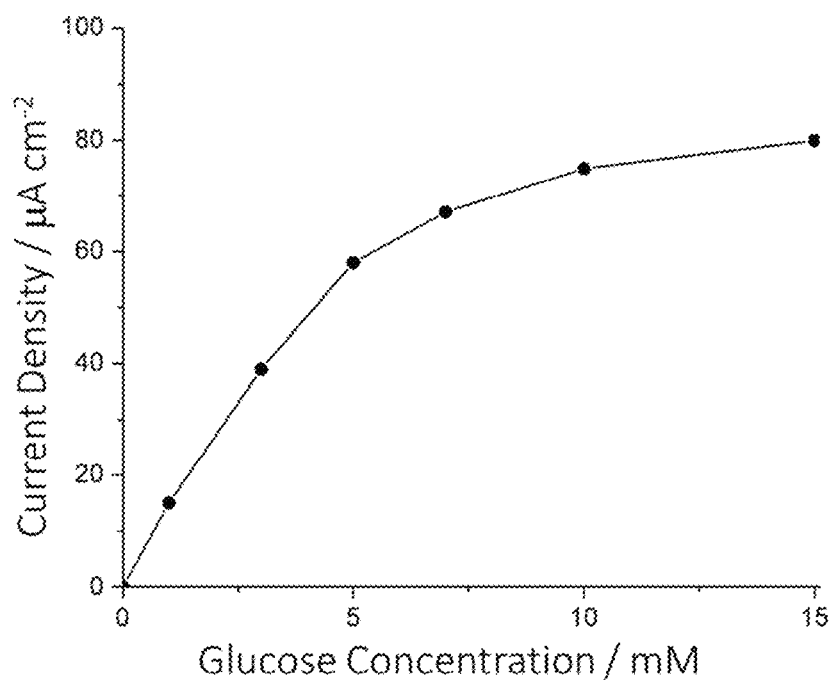
FIG. 7 illustrates the titration detection of glucose concentration (0-15 mM) in a simulated body fluid environment using the DI-GDH enzymatic electrochemical system provided in embodiments of the present invention. It depicts the relationship between titrated glucose concentration and the corresponding reaction current.

Detection of Glucose Concentration (0-15 mM) in a Near-Human Serum Environment:

The three-electrode electrolytic cell described in Example 1 was placed in an anaerobic glove box. Under the control of the Ivium electrochemical workstation, a constant voltage scan at −0.2 V was conducted, with magnetic stirring at 800 rpm. After the reaction started and the current stabilized, a concentrated glucose solution was added using a syringe for titration, increasing the glucose concentration in the reaction liquid from 0-15 mM. The change in reaction rate was reflected by the reaction current, corresponding to the change in glucose concentration. The relationship between titrated glucose concentration and reaction current was plotted (as shown in FIG. 7); this graph reflects a good correspondence between current and concentration within the glucose concentration range in the simulated body fluid environment, generated by the mixed coenzymes NAD/NADP.

Example 5

17.3 g of high-conductivity graphite powder, 21.4 g of polyacrylic acid resin, 1 g of organic silicon defoamer, and 60.3 g of ethyl acetate are thoroughly mixed. The mixture is stirred at high speed at 2500 rpm for 5 hours to obtain a base ink. 40 g of zinc oxide is added to the base ink, and after mixing well, a composite ink is obtained. The composite ink is screen printed onto an ITO film-supported substrate using a 500-mesh screen and cured at 60° C. for 5 hours to obtain the working electrode.

The above content further elaborates the invention in conjunction with specific preferred embodiments. It should not be understood that the concrete implementation of the invention is limited to these descriptions. For those skilled in the art, various simple deductions or substitutions can be made without departing from the concept of the invention, and they should be considered within the scope of protection of the invention.

Example 6

Preparation of Enzyme Electrode

The NAD-type DI (5 μL) and the NAD-type Glycerol dehydrogenase (GD) (25 μL) were mixed. This mixture was uniformly applied to a working electrode prepared as described in Example 5 (surface area 2.8 cm$^2$), left to incubate for 25 minutes, then rinsed with pH 8 TAPS buffer to wash off the surface enzyme solution, obtaining a working electrode plate loaded with a mix of NAD-dependent DI and GD.

Using the above-mentioned DI and GD-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of pH 8 TAPS buffer with an additional 10 mM of glycerol added.

Live Detection of Glycerol

Figure 9:
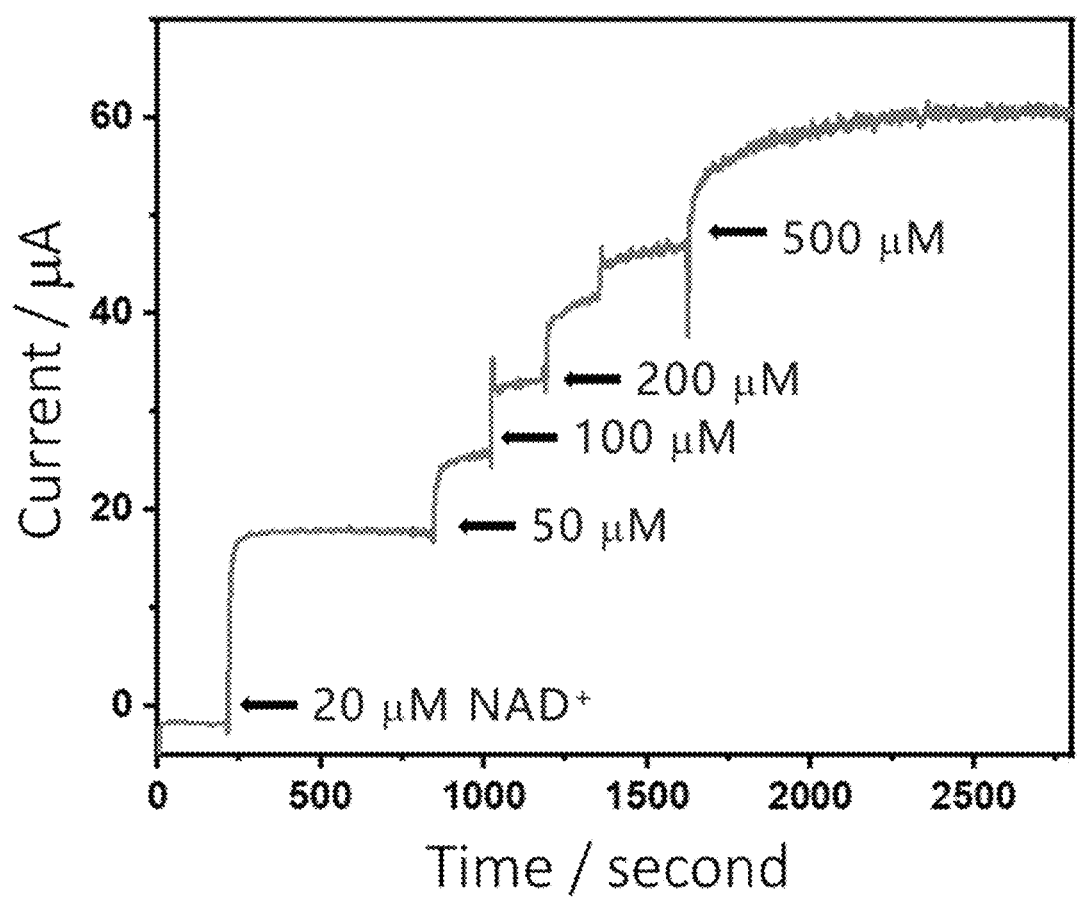
FIG. 9 illustrates the titration of $NAD^+$ in glycerol detection using the electrode manufacturing technology. The detection of glycerol (10 mM) is reflected in the form of current through the DI-glycerol dehydrogenase electrochemical system provided in embodiments of the present invention.

The three-electrode electrolytic cell described in Example 1 was placed in an anaerobic glove box. Under the control of the Ivium electrochemical workstation, a constant voltage scan at −0.1 V was conducted, with magnetic stirring at 800 rpm. After the reaction started and the current stabilized, a concentrated NAD$^+$ solution was added using a syringe for titration, increasing the glycerol concentration in the reaction liquid from 0 to 500 μM. The change in reaction rate was reflected by the current, indicating the reaction of GD oxidizing glycerol existed in the solution (FIG. 9). This figure reflects a fast and distinguishable detection of glycerol with the technique of enzyme electrode manufacturing. This example shows the potential generalized usage of the electrode as a detector for various species with different enzymes.

Example 7

Preparation of Enzyme Electrode

The NAD-type DI (5 μL) and the NAD-type D-Lactate dehydrogenase (LD) (25 μL) were mixed. This mixture was uniformly applied to a working electrode prepared as described in Example 5 (surface area 2.8 cm$^2$), left to incubate for 25 minutes, then rinsed with pH 8 TAPS buffer to wash off the surface enzyme solution, obtaining a working electrode plate loaded with a mix of NAD-dependent DI and LD.

Using the above-mentioned DI and LD-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of pH 8 TAPS buffer with an additional 10 mM of lactic acid added.

Live Detection of Lactic Acid

Figure 10:
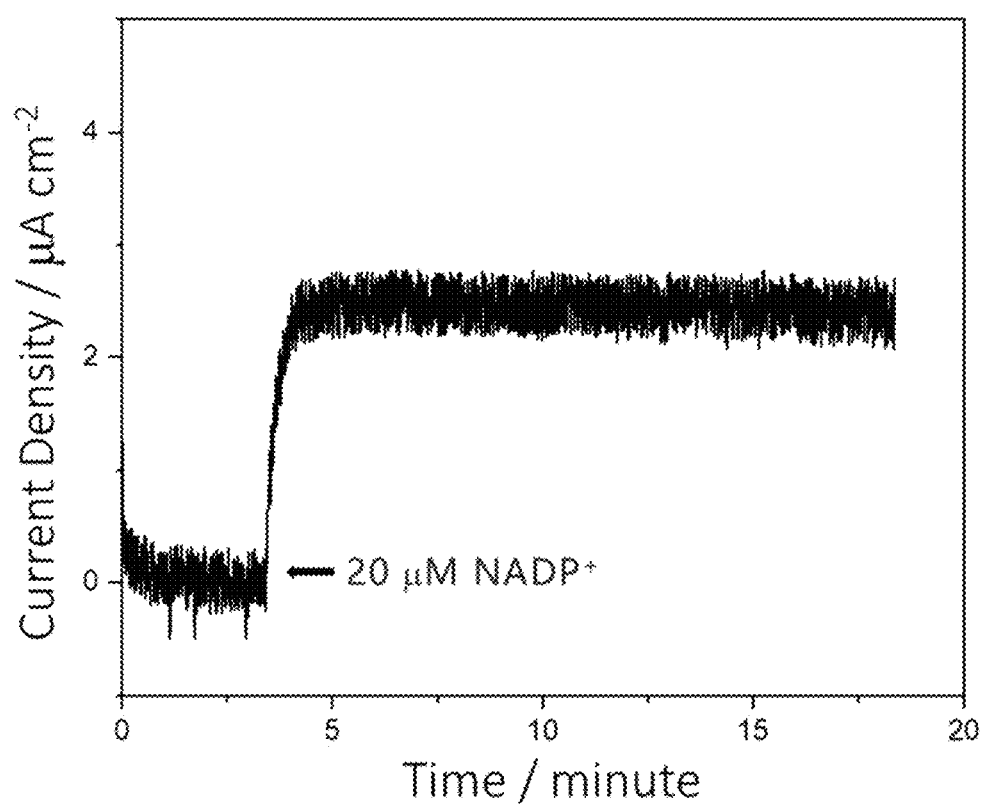
FIG. 10 illustrates the titration of NADP$^+$ during lactate detection using the electrode manufacturing technology provided in embodiments of the present invention. The detection of lactate (10 mM) is reflected in the form of current through the DI-lactate dehydrogenase electrochemical system provided in embodiments of the present invention.

The three-electrode electrolytic cell described in Example 1 was placed in an anaerobic glove box. Under the control of the Ivium electrochemical workstation, a constant voltage scan at −0.1 V was conducted, with magnetic stirring at 800 rpm. After the reaction started and the current stabilized, a concentrated NAD$^+$ solution was added using a syringe to a final concentration of 20 μM in the cell. The change in reaction rate was reflected by the reaction current, indicating the reaction of LD oxidizing lactic acid existed in the solution (FIG. 10). This figure reflects a fast and distinguishable detection of lactic acid with the technique of enzyme electrode manufacturing. This example shows the potential generalized usage of the electrode as a detector for various species with different enzymes.

Comparative Example 1

Figure 8:
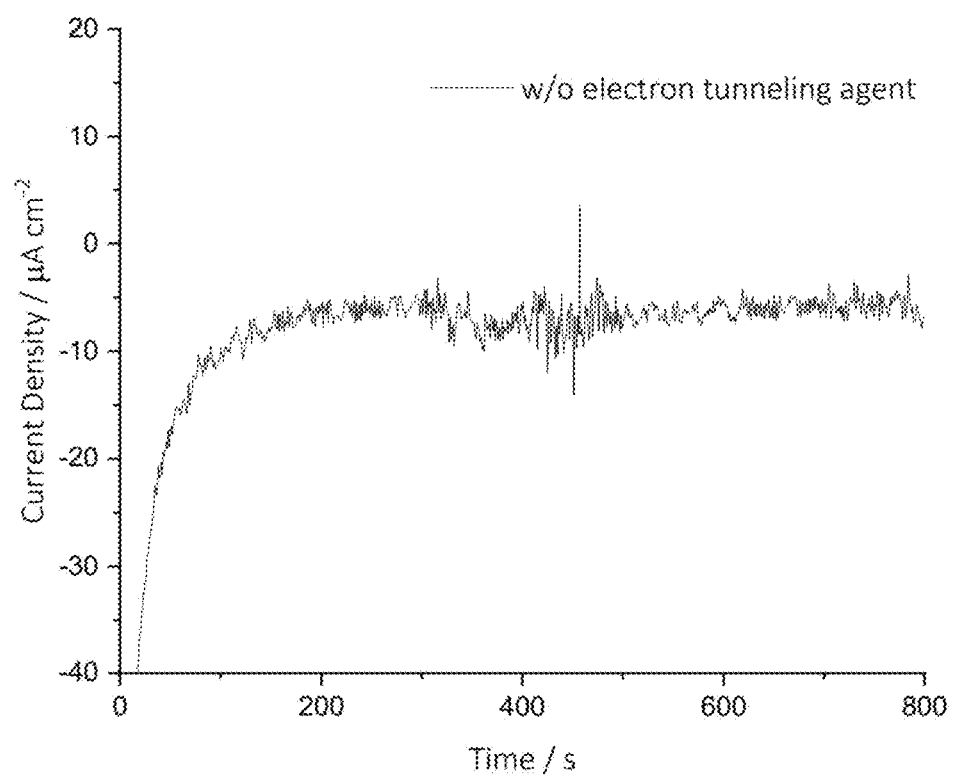
FIG. 8 depicts the titration detection of glucose using the working electrode of Comparative Example 1 in an anaerobic environment.

The only difference in the preparation method of the working electrode from that of Example 5 is the absence of zinc oxide as an electron tunnelling agent. The response to glucose was tested following the method of Example 1, conducted inside an anaerobic glove box. In FIG. 8, under an anaerobic environment, the response current after the addition of glucose is shown. It can be observed that there is no significant change in the current upon the addition of glucose, indicating that the working electrode without an electron tunnelling agent cannot achieve the detection of glucose.

Example 8

Preparation of Enzyme Electrode

The NAD-type DI (5 μL) and the NAD-type β-hydroxybutyrate dehydrogenase (HBD) (25 μL) were mixed. This mixture was uniformly applied to a working electrode prepared as described in Example 5 (surface area 2.8 cm$^2$), left to incubate for 25 minutes, then rinsed with pH 8 TAPS buffer to wash off the surface enzyme solution, obtaining a working electrode plate loaded with a mix of NAD-dependent diaphorase (DI) and HBD.

Using the above-mentioned diaphorase (DI) and HBD-loaded working electrode plate as the working electrode, a platinum plate as the counter electrode, and Ag/AgCl (3 M KCl) as the reference electrode, a three-electrode electrochemical cell was assembled. The electrolyte in the cell was 6 mL of of pH 7.4 simulated body fluid SBF with an additional 20 μM of NAD$^+$ added.

Live Detection of β-Hydroxybutyrate (HB)

Figure 11:
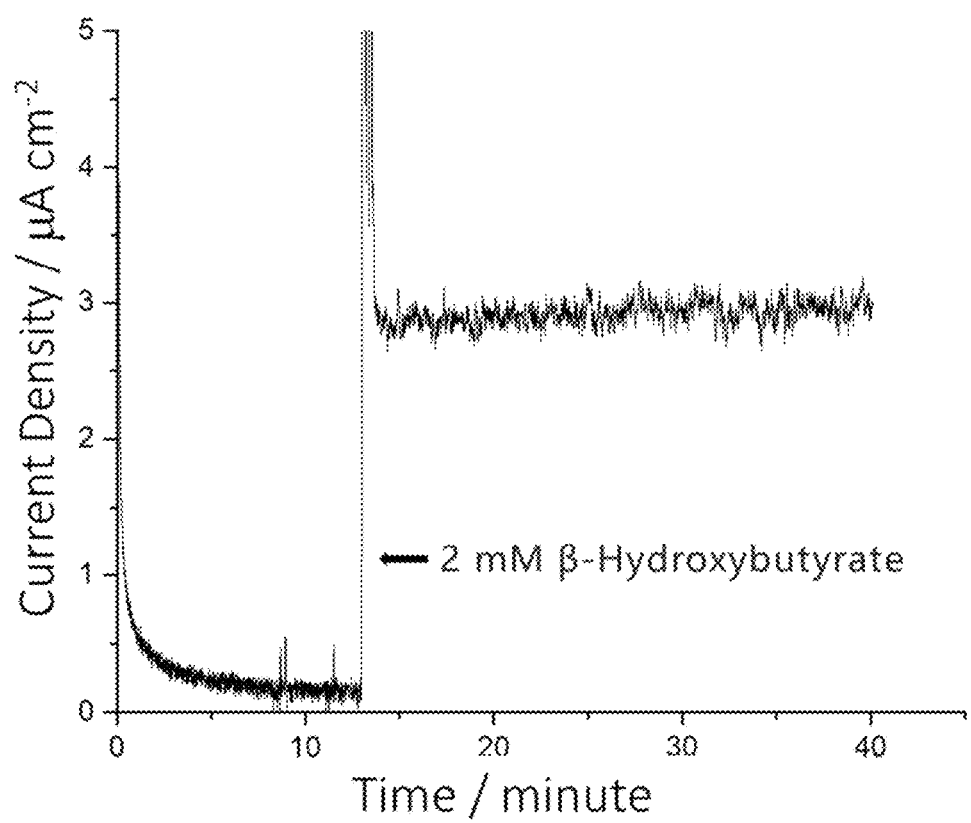
FIG. 11 represents the concentration titration of β-hydroxybutyric acid (HB) in Example 8.

The three-electrode electrolytic cell described in Example 1 was placed in an anaerobic glove box. Under the control of the Ivium electrochemical workstation, a constant voltage scan at 0 V was conducted, with magnetic stirring at 800 rpm. After the reaction started and the current stabilized, a concentrated HB solution was added using a syringe to a final concentration of 2 mM in the cell. The change in reaction rate was reflected by the reaction current, indicating the reaction of HBD oxidizing HB existed in the solution (FIG. 11). This figure reflects a fast and distinguishable detection of β-Hydroxybutyrate with the technique of enzyme electrode manufacturing. This example shows the potential generalized usage of the electrode as a detector for various species with different enzymes.

What is claimed is:

1. An enzymatic electrode system, characterized by comprising:
   a working electrode, a counter electrode, and an optional reference electrode;
   the working electrode comprises an electrode support substrate and a conductive substrate located at the top of the electrode support substrate, wherein the conductive substrate has a porous structure; a surface or interior of the conductive substrate contains oxidoreductases, coenzyme reductases, and optional coenzymes; wherein during detection, electrons are transferred directly between the conductive substrate and the coenzyme reductases without an electron mediator: a distance betweem tje cpmemzu,e redictases and the conductive substrate is less than 15 Å.

2. According to the enzymatic electrode system described in claim 1, it is characterized in that the optional coenzyme is selected from one or more of NAD (H), NADP (H), or FAD.

3. According to the enzymatic electrode system described in claim 2, it is characterized in that the oxidoreductase is at least one of glucose dehydrogenase, lactate dehydrogenase, alcohol dehydrogenase, aldehyde dehydrogenase, or ketone dehydrogenase.

4. According to the enzymatic electrode system described in claim 3, it is characterized in that the oxidoreductase is at least one of NAD-dependent glucose dehydrogenase, NADP-dependent glucose dehydrogenase, or FAD-dependent glucose dehydrogenase.

5. According to the enzymatic electrode system described in claim 1, it is characterized in that the coenzyme reductase is flavoprotein.

6. According to the enzymatic electrode system described in claim 5, it is characterized in that the flavoprotein is diaphorase (DI).

7. According to the enzymatic electrode system described in claim 1, it is characterized in that the conductive substrate is selected from ITO (indium tin oxide), ATO (antimony tin oxide), AZO (aluminum-doped zinc oxide), graphene, carbon nanotubes, alumina-silica, gold electrode, silver electrode, or doped nanoelectrodes made of conductor or semiconductor materials.

8. According to the enzymatic electrode system described in claim 1, it is characterized in that a pore size of the porous structure is in a range of 20 nm to 100 nm.

9. According to the enzymatic electrode system described in claim 1, it is characterized in that a thickness of the conductive substrate is in a range of 100 nm to 5000 nm.

10. According to the enzymatic electrode system described in claim 1, it is characterized in that the oxidoreductases, coenzyme reductases, and optional coenzymes are placed on the surface or interior of the conductive substrate to form a conductive layer; a method of forming the conductive layer includes at least one of electrophoretic deposition, vacuum spraying, biotechnology, chemical coupling, or screen printing.

11. According to the enzymatic electrode system described in claim 1, it is characterized in that the oxidoreductases, coenzyme reductases, and optional coenzymes are co-immobilized through adsorption, covalent attachment, entrapment or electrostatic adsorption, fixed on the surface or interior of the conductive substrate.

12. According to the enzymatic electrode system described in claim 1, it is characterized in that the conductive substrate comprises a base ink and nanoscale oxides, wherein the nanoscale oxides serve as electron tunnelling agents, allowing electrons to transfer directly from the conductive substrate to the coenzyme reductase.

13. According to the enzymatic electrode system described in claim 12, it is characterized in that the base ink comprises conductive particles, binders, defoamers, and dispersants.

14. According to the enzymatic electrode system described in claim 12, it is characterized in that the conductive substrate is produced by screen printing a composite ink formed by the base ink and the nanoscale oxides.

15. According to the enzymatic electrode system described in claim 12, it is characterized in that the nanoscale oxides include at least one of aluminum oxide, zinc oxide, iron oxide, silicon dioxide, calcium oxide, magnesium oxide, tin oxide, indium tin oxide, aluminum-doped zinc oxide, or antimony tin oxide, and a size of the nanoscale oxides is in a range of 20 nm to 1000 nm.

16. A detection system comprising:
An enzymatic electrode system as described in claim 1;
A potentiostat for generating current in the enzymatic electrode system; and
A current measurement device for measuring a current generated in the enzymatic electrode system.

17. According to the enzymatic electrode system described in claim 1, wherein the conductive substrate comprises nanoscale oxides serve as electron tunnelling agents, enabling direct electron transfer from the conductive substrate to the coenzyme reductase without electron mediators.

18. According to the enzymatic electrode system described in claim 1, wherein during detection, the oxidoreductase reacts with a target analyte to oxidize the target analyte to a corresponding oxidized product and transfers electrons to a coenzyme, the coenzyme reductase converts a reduced form of the coenzyme back to an oxidized form of the coenzyme.

19. According to the enzymatic electrode system described in claim 18, wherein the oxidoreductase comprises glucose dehydrogenase, the coenzyme comprises $NAD(P)^+$, and the coenzyme reductase comprises diaphorase;
wherein during detection, the glucose dehydrogenase reacts with glucose to oxidize the glucose to gluconic acid and transfers electrons to the $NAD(P)^+$, reducing the $NAD(P)^+$ to $NAD(P)H$; the $NAD(P)H$ is then oxidized back to the $NAD(P)^+$ under the diaphorase.

* * * * *